US008747890B2

(12) United States Patent
Helson

(10) Patent No.: US 8,747,890 B2
(45) Date of Patent: Jun. 10, 2014

(54) INTRAVENOUS INFUSION OF CURCUMIN AND A CALCIUM CHANNEL BLOCKER

(75) Inventor: Lawrence Helson, Quakertown, PA (US)

(73) Assignee: Signpath Pharma Inc., Quakertown, PA (US)

( * ) Notice: Subject to any disclaimer, the term of this patent is extended or adjusted under 35 U.S.C. 154(b) by 347 days.

(21) Appl. No.: 12/949,897

(22) Filed: Nov. 19, 2010

(65) Prior Publication Data

US 2011/0117186 A1 May 19, 2011

Related U.S. Application Data

(60) Provisional application No. 61/262,745, filed on Nov. 19, 2009.

(51) Int. Cl.
*A61K 9/127* (2006.01)
(52) U.S. Cl.
USPC .......................................... 424/450; 424/497
(58) Field of Classification Search
USPC ......................................... 424/450, 489, 497
See application file for complete search history.

(56) References Cited

U.S. PATENT DOCUMENTS

| 6,143,276 | A | 11/2000 | Unger | |
|---|---|---|---|---|
| 7,507,864 | B2 | 3/2009 | Miller et al. | |
| 7,723,515 | B1 | 5/2010 | DiMauro | |
| 7,871,609 | B2 | 1/2011 | Ziff et al. | |
| 7,968,115 | B2 | 6/2011 | Kurzrock et al. | |
| 8,062,663 | B2 * | 11/2011 | Wang et al. | 424/450 |
| 2001/0051184 | A1 * | 12/2001 | Heng | 424/461 |
| 2005/0181036 | A1 | 8/2005 | Aggarwal et al. | |
| 2005/0266067 | A1 | 12/2005 | Sengupta et al. | |
| 2008/0075671 | A1 | 3/2008 | Di Mauro | |
| 2008/0103213 | A1 | 5/2008 | Kurzrock et al. | |
| 2008/0253961 | A1 * | 10/2008 | Braden et al. | 424/1.11 |
| 2009/0143433 | A1 | 6/2009 | Hendrix | |
| 2010/0151000 | A1 * | 6/2010 | Thomas et al. | 424/450 |
| 2012/0003177 | A1 * | 1/2012 | Shen et al. | 424/78.31 |

FOREIGN PATENT DOCUMENTS

| WO | 2000070949 A1 | 11/2000 |
|---|---|---|
| WO | 2006061101 A2 | 6/2006 |
| WO | 2008045534 A2 | 4/2008 |
| WO | 2008128123 A1 | 10/2008 |
| WO | 2009051837 A2 | 4/2009 |
| WO | 2010033692 A1 | 3/2010 |
| WO | 2011119588 A1 | 9/2011 |

OTHER PUBLICATIONS

Aggarwal, et al., "The Molecular Targets and Therapeutic Uses of Curcumin in Health and Disease," (2006), Springer, 515 pages.
Bentzen, Peter J., et al., "Curcumin Induced Suicidal Erythrocyte Death," Cellular Physiology and Biochemistry, (2007), 19:153-164.
Bisht, Savita, et al., "Polymeric Nanoparticle-Encapsulated Curcumin ("Nanocurcumin"): A Novel Strategy for Human Cancer Therapy," Journal of Nanobiotechnology, (2007), 18 pages.
Everett, Peter C., et al., "Preclinical Assessment of Curcumin as a Potential Therapy for B-CLL," American Journal of Hematology, (2006), 8 pages.
International Search Report and Written Opinion for PCT/US2010/057332, dated Aug. 2, 2011, 12 pages.
Li, Lan, et al., "Liposome-Encapsulated Curcumin in Vitro and in Vivo Effects on Proliferation, Apoptosis, Signaling, and Angiogenesis," Cancer, 104:1322-1331.
Logan-Smith, Melanie J., et al., "Curcumin, a Molecule that Inhibits the Ca2+ -ATPase of Sarcoplasmic Reticulum but Increases the Rate of Accumulation of Ca2+," The Journal of Biological Chemistry, (2001), vol. 276, No. 50, pp. 46905-46911.
Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.
Mukerjee, Anindita, et al., "Formulation, Characterization and Evaluation of Curcumin-Loaded PLGA Nanospheres for Cancer Therapy," (2009), Anticancer Research 29:3867-3876.
Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.
Abel, Ted., et al., "Epigenetic Targets of HDAC Inhibition in Neurodegenerative and Psychiatric Disorders," Current Opinion in Pharmacology, (2008), vol. 8, pp. 57-64.
Anderson, P., et al., "The Hippocampus Book," Oxford University Press, 2006, 102 pages.
Ataie, Amin, et al., "Neuroprotective Effects of the Polyphenolic Antioxidant Agnet, Curcumin, Against Homocysteine-Induced Cognitive Impairment and Oxidative Stress in the Rat," Pharmacology, Biochemistry and Behavior, (2010), vol. 96, pp. 378-385.
Bala, Kiran, et al., "Neuroprotective and Anti-Aging Effects of Curcumin in Aged Rat Brain Regions," Biogerontology, (2006), vol. 7, pp. 81-89.
Garcia-Alloza, M., et al., "Curcumin Labels Amyloid Pathology in Vivo, Disrupts Existing Plaques, and Partially Restroes distorterneurites in an Alzheimer Mouse Model," Journal of Neurochemistry, (2007), vol. 102, pp. 1095-1104.
Kessler, Ronald C., et al., "Posttraumatic Stress Disorder in the national Comorbidity Survey," Archives of General Psychiatry, vol. 52, No. 12, pp. 1049-1060.

(Continued)

*Primary Examiner* — Gollamudi Kishore
(74) *Attorney, Agent, or Firm* — Edwin S. Flores; Chainey P. Singleton; Chalker Flores, LLP

(57) ABSTRACT

Compositions and methods for treating systemic diseases by intravenous administration of formulations of synthesized curcumin (diferuloylmethane) and concomitantly a calcium channel blocker to human subjects with neoplastic and neurodegenerative diseases are disclosed herein. The diseases are treated by prolonged administration of sub-optimal doses of liposomal curcumin or polymeric nanocurcumin or the sustained release curcumin from PLGA nanocurcumin at dosages below systemic hemolytic thresholds concomitantly with or without calcium channel blockers.

2 Claims, No Drawings

(56) References Cited

OTHER PUBLICATIONS

Kim, So Jung, et al., "Curumin Stimulates Proliferation of Embryonic Neural Progenitor Cells and Neurogenesis in the Adult Hippocampus," The Journal of Biological Chemistry, May 23, 2008, vol. 283, No. 21, pp. 14497-14505.

Li, Yu-Cheng, et al., "Antidepressant-Like Effects of Curcumin on Serotonergic Receptor-Coupled AC-cAMP Pathway in Chronic Unpredictable Mild Stress of Rats," Progress in Neuro-Psychophamacoloby & Biological Psychiatry, (2009), vol. 33, pp. 435-449.

Pitman, Roger K., et al., "Conceptually Driven Pharmacologic Approaches to Acute Trauma," CNS Spectrums, Feb. 2005, vol. 10, No. 2, pp. 99-106.

Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.

Rui, Pan, et al., "Curcumin Improves Learning and Memory Ability and its Neuroprotective Mechanism in Mice," Chin. Med. J., (2008), vol. 121, No. 9, pp. 832-839.

Rusinek, Henry, et al., "Hippocampal Blood Flow in Normal Aging Measured with Arterial Spin Lavelin at 3T," Magnetic Resonance in Medicine, (2011), 65:128-137.

Segman, Rh., et al., "Association Between the Dopamine Transporter Gene and Posttraumatic Stress Disorder," Molecular Psychiatry, (2002), vol. 7, pp. 903-907.

Segman, RH., et al., "Peripheral Blood Mononuclear Cell Gene Expression Profiles Identify Emergent Post-Traumatic Stress Disorder Among Trauma Survivors," Molecular Psychiatry, (2005), vol. 10, pp. 500-513.

Stein, Murray B., et al., "Genetic and Environmental Influences on Trauma Exposure and Posttraumatic Stress Disorder Symptoms: A Twin Study," Am. J. Psychiatry, Oct. 2002, vol. 159, No. 10, pp. 1675-1681.

Xu, Ying, et al., "Curcumin Reverses Impaired Hippocampal Neurogenesis and Increases Serotonin Receptor 1A mRNA and Brain-Derived Neurotrophic Factor Expression in Chronically Stressed Rats," Brain Research, (2007), 1162, pp. 9-18.

Fahn, Stanlex, "Medical Treatment of Parkinson's Disease," Journal of Neurology, 1998, 245 (Supplement 3): P15-P24.

Marino, Silvia, et al., "Sertaline in the Treatment of Depressive Disorders in Patients with Parkinson's Disease," Neurological Sciences, Nov. 2008, 29:391-395.

Tonnesen, Hanne, H., et al, "Studies on curcumin and curcuminoids: XXV. Inhibition of primaquine-induced lysis of human red blood cells by curcumin," International Journal of Pharmaceutics 110 (1994) 161-167.

Extended European Search Report and Europeean Search Opinion for EPO 10832224.9 dated Feb. 26, 2013.

* cited by examiner

INTRAVENOUS INFUSION OF CURCUMIN AND A CALCIUM CHANNEL BLOCKER

CROSS-REFERENCE TO RELATED APPLICATIONS

This application claims priority to U.S. Provisional Application Ser. No. 61/262,745, filed Nov. 19, 2009, the contents of which are incorporated by reference herein in its entirety.

TECHNICAL FIELD OF THE INVENTION

This invention relates in general to the field of treatment of neoplastic and neurodegenerative diseases, and more particularly to the intravenous administration of formulations of synthesized curcumin (diferuloylmethane) and concomitantly a calcium channel blocker to human subjects in need of treatment against neoplastic and neurodegenerative diseases. Particular reference is made to the prolonged administration of liposomal curcumin, or polymeric nanocurcumin or to the sustained release of curcumin from PLGA nanocurcumin at dosages below systemic hemolytic thresholds concomitantly with calcium channel blockers.

STATEMENT OF FEDERALLY FUNDED RESEARCH

None.

REFERENCE OF A SEQUENCE LISTING

None.

BACKGROUND OF THE INVENTION

Without limiting the scope of the invention, its background is described in connection with the use and dosage forms of chemotherapeutic agents and agents for treating neurodegenerative diseases, including curcumin, curcumin analogues, and derivatives.

Curcumin has been reported to react negatively with growth receptors such as epidermal growth factor, bFGF, cytokine stimuli such as tumor necrosis factor and elements of signaling pathways including key components of proliferation; Survivin, Akt, DNA telomerase, BCL-2, and activators of NF-kB[5]. In both tumoral and normal tissues it acts as an antioxidant and contributes towards maintaining the redox potential of cells. Oral administration as an extract of the turmeric plant has been used in traditional medicine for over two thousand years and is reported to be devoid of toxicity and concomitantly systemic therapeutic activity mainly because of water insolubility, intestinal and hepatic inactivation causing negligible bioavailability to tissues beyond the gastrointestinal tract. To overcome these limitations, parenteral intravenous curcumin formulations with liposomes[2], polymers[3] (n-isopropylacrylamide, N-vinylpyrrolidione and acrylic acid) and polylactic glycolic acid copolymer[4] are being developed.

U.S. Pat. No. 7,723,515 issued to Dimauro (2010) discloses the use of methylene blue, a curcumin hybrid for treating Alzheimer's Disease. The '515 patent relates to the intranasal administration of a formulation comprising an effective amount of curcumin to the olfactory mucosa across the cribriform plate and into the brain in order to treat a neurodegenerative disease, such as AD.

U.S. Patent Application No. 20060067998 (Kurzrock et al. 2006) provides compositions and methods for the treatment of cancer, including pancreatic cancer, breast cancer and melanoma, in a human patient. The methods and compositions of the present invention employ curcumin or a curcumin analogue encapsulated in a colloidal drug delivery system, preferably a liposomal drug delivery system. Suitable colloidal drug delivery systems also include nanoparticles, nanocapsules, microparticles or block copolymer micelles. The colloidal drug delivery system encapsulating curcumin or a curcumin analogue is administered parenterally in a pharmaceutically acceptable carrier.

SUMMARY OF THE INVENTION

The present invention includes compositions and methods for treating systemic diseases characterized by abnormal cellular stimuli, pathologic responses to oxidants, cytokines, and growth factors; leading to abnormal activation of signaling pathways, protein synthesis and unfettered death or proliferation. Blocking these pathways at one or more sites using curcumin was selected for use in a therapeutic method.

In one embodiment the present invention discloses a formulated pharmaceutical composition comprising: a therapeutically effective amount of a synthesized curcumin (diferuloylmethane), wherein the synthesized curcumin is enveloped by a polylactic glycolic acid (PLGA) copolymer, a layer of lipids to form a liposome, conjugated to one or more polymers or any combinations thereof; and one or more calcium channel blockers, wherein the composition mitigates a curcumin induced red blood cell (RBC) hemolysis. The composition of the present invention is adapted for an intravenous administration in a human subject for a treatment of one or more proliferative selected from the group consisting of neoplastic disorders, neurodegenerative diseases, drug induced tardif dyskinesia, parasitic diseases and abnormal ophthalmic disorders such as cataract and macular degeneration. In specific aspects of the present invention the neoplastic disorders comprise breast cancer, uterine cancer, cervical cancer, ophthalmic tumors, brain tumors, and pancreatic cancer and the neurodegenerative diseases comprise neuropathologic disorders, Parkinson's disease, Alzheimer's disease (AD), senile dementia, vascular dementias, Pick's disease, and Creutzfeldt-Jacobs disease.

In another aspect the one or more calcium channel blockers are selected from the group consisting of verapamil, ethylisopropylameloride, niflamic acid, NPPB, dihydropyridines, phenylalkylamines, Benzothiozepines, Diltiazem, nonselective blockers comprising mibefradil, bepridil, fendeline, fluspirilene, catecholamines, and erythropoietin agents. In yet another aspect the calcium channel blockers are administered prior to or concomitantly with the synthesized curcumin. In one aspect the composition comprises one or more optional pharmaceutically acceptable excipients, diluents, extended or controlled release agents, lubricants, preservatives or any combinations thereof.

In a related aspect the polymer is a biodegradable polymer selected from the group consisting of polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), copolymers, terpolymers, and combinations or mixtures thereof. More specifically, the polymer is an acrylic acid, a vinylpyrolidinome, a N-isopropylacrylamide or combinations and modifications thereof. In another related aspect the synthesized curcumin comprises curcumin, curcumin analogues, curcumin derivatives, and any combinations or modifications thereof.

In another embodiment the present invention provides a method comprising intravenous administration to a subject of a therapeutically effective amount of a formulated composition of synthesized curcumin (diferuloylmethane), wherein the synthesized curcumin is enveloped by a polylactic glycolic acid (PLGA) copolymer, a layer of lipids to form a liposome, conjugated to one or more polymers or any combinations thereof in combination with one or more calcium channel blockers to mitigate intravenous curcumin induced red blood cell (RBC) hemolysis. The polymer used in the method of the present invention is an acrylic acid, a vinylpyrolidinome, a N-isopropylacrylamide or combinations and modifications thereof. In one aspect the calcium channel blockers are administered prior to or concomitantly with the synthesized curcumin. In another aspect the one or more calcium channel blockers are selected from the group consisting of verapamil, ethylisopropylameloride, niflamic acid, NPPB, dihydropyridines, phenylalkylamines, Benzothiozepines, Diltiazem, nonselective blockers comprising mibefradil, bepridil, fendeline, fluspirilene, catecholamines, and erythropoietin agents.

In yet another embodiment the present invention provides a method of treating a subject afflicted with one or more proliferative disorders comprising the steps of: identifying the subject in need of treatment against the one or more proliferative disorders; and administering topically or systemically a therapeutically effective amount of one or more formulations of a synthesized curcumin, wherein the formulations comprise a polylactic glycolic acid (PLGA-curcumin) copolymer enveloped curcumin, a liposomal curcumin or a polymer conjugated curcumin (nanocurcumin), wherein the formulation is administered in combination with a calcium channel blocker and is administered in a sustained and specific manner.

In one aspect the one or more proliferative diseases comprise breast, uterine cervical, ophthalmic and pancreatic cancer. In another aspect the formulation mitigates a curcumin induced red blood cell (RBC) hemolysis. In a related aspect the liposomal curcumin or nanocurcumin is infused continuously for 1-72 hours weekly for four weeks, or for 24 hours every other day weekly for 12 doses in combination with a calcium channel blocker. In another aspect the PLGA-curcumin is infused for 1 hour weekly for four weeks in combination with a calcium channel blocker. In yet another aspect the calcium channel blocker is selected from the group consisting of verapamil, ethylisopropylameloride, niflamic acid, NPPB, dihydropyridines, phenylalkylamines, Benzothiozepines, Diltiazem, nonselective blockers comprising mibefradil, bepridil, fendeline, fluspirilene, catecholamines, and erythropoietin agents. In a specific aspect the polymer is an acrylic acid, a vinylpyrolidinome, a N-isopropylacrylamide or combinations and modifications thereof.

Embodiments of the present invention disclose a method of treating one or more diseases or conditions in a subject comprising the steps of: (i) identifying the subject in need of treatment against the disease or the condition and (ii) administering a therapeutic effective amount of at least one formulation of a synthesized curcumin selected from the group consisting of polylactic glycolic acid (PLGA-curcumin) copolymer enveloped curcumin, a liposomal curcumin or a polymer conjugated curcumin (nanocurcumin) in combination with a calcium channel blocker selected from the group consisting of verapamil, ethylisopropylameloride, niflamic acid, NPPB, dihydropyridines, phenylalkylamines, Benzothiozepines, Diltiazem, nonselective blockers comprising mibefradil, bepridil, fendeline, fluspirilene, catecholamines, and erythropoietin agents. The disease or the condition described hereinabove comprises proliferative diseases selected from the group consisting of breast cancer, uterine cancer, cervical cancer, ophthalmic tumors, brain tumors, pancreatic cancer, neuropathologic disorders, Parkinson's disease, drug induced tardif dyskinesia, parasitic diseases, and abnormal ophthalmic disorders such as cataract and macular degeneration. The method as described herein, further comprising the step of adding curcumin formulations and a calcium channel blocker to autologous bone marrow stem cell or peripheral blood stem cell preparations prior to transplant into a recipient in order to eliminate viable tumor cell contamination.

In another embodiment the present invention provides a method for treating a tumor in a human subject comprising the step of: identifying the subject in need of the treatment against the tumor; and administering a therapeutically effective amount of a polylactic glycolic acid (PLGA-curcumin) curcumin conjugate with or without a calcium channel blocker directly into the tumor for treating the tumor. In one aspect of the tumor treating method of the present invention the curcumin is a synthesized curcumin, comprising curcumin, a curcumin analogue, a curcumin derivative, and any combinations or modifications thereof. In another aspect the conjugate is adapted for administration in situ into a breast for treatment of a ductal carcinoma, into an aqueous humor of an eye for the treatment of a retinoblastoma or uveal melanoma, for intravesicular administration for the treatment of a bladder cancer or for direct application to an uterine cervix marked by a dysplasia or a cancer.

Embodiments of the present invention also disclose a method of treating an ophthalmic tumor, an age related condition comprising macular degeneration and cataract or both in a subject comprising the step of: identifying the subject in need of treatment against the tumor or the age related condition; and administering a therapeutically effective amount of a composition adapted for ocular administration into the eye of the subject, wherein the composition comprises a polylactic glycolic acid (PLGA-curcumin) curcumin conjugate, a polymer conjugated curcumin (nanocurcumin) or both with or without a calcium channel blocker for the treatment of the tumor or the age related condition. The curcumin used in the treatment method described above is a synthesized curcumin, comprising curcumin, a curcumin analogue, a curcumin derivative, and any combinations or modifications thereof.

The invention provides a method for treating systemic disorders in humans. The method comprises administering a pharmaceutical composition intravenously as an intermittent continuous infusion or sustained release during a 28 day treatment cycle; which may be repeated depending upon tolerance, and therapeutic need. By combining curcumin with a calcium channel blocker hemolytic effects of curcumin are mitigated. The compositions for use with the methods of the present invention include, e.g., different formulations that enclose an effective amount of curcumin, increases aqueous solubility, enhances delivery to pathologic tissues, and protect curcumin from hepatic inactivating enzymes. In mice, curcumin solubility limits the intravenous injectible volume to a maximum dose of 250 mg/M$^2$, which does not indicate the upper limit of dosage. Liposomal curcumin at 125 mg/M$^2$ significantly inhibited growth of human pancreatic xenografts in mice without toxicity[8]. A 140 mg/M$^2$/dose would offer a similar dose intensity in humans because of smaller human body surface area relative to weight. The maximum tolerated dose marked by a brief reversible limited episode of hemolysis and hematuria in four out of five 10 kg dogs infused over one hour was 440 mg/M². An 800 mg/M² single dose in dogs induced irreversible life-threatening hemolysis. In an 80 kg human with a 5 liter blood volume, a 440 mg/M² intravenous infusion would exceed the maximum tolerated dose. To avoid toxicity this invention teaches the intravenous route of administration of curcumin formulations should be limited to low dosages at slow infusion rates for liposomal curcumin, and polymeric nanocurcumin or a sustained release of curcumin from a PLGA-nanocurcumin formulations in combination with a calcium channel blocker.

BRIEF DESCRIPTION OF THE DRAWINGS

None.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "curcumin" as used herein refers to (diferuloyl methane; 1,7-bis(4-hydroxy-3-methoxyphenyl)-1,6-heptadiene-3,5-dione) is a naturally occurring compound which is the main coloring principle found in the rhizomes of the plant *Curcuma longa* (U.S. Pat. No. 5,679,864 (Krackov et al.)). The term also includes any of those structurally similar compounds encompassed by the term as understood by those skilled in the art. The "curcumin" can be natural or synthetic, and it can be present in any degree of purity wherein it retains its characteristic coloring characteristics.

The term "calcium-channel blocker" or "$Ca^{2+}$-channel blocker" refers to one of a class of pharmacological agents, also known as calcium antagonists, which inhibit the transmembrane flux of calcium ($Ca^{2+}$) ions. "Calcium channel blockers" are also known as calcium ion influx inhibitors, slow channel blockers, calcium ion antagonists, calcium channel antagonist drugs and as class IV antiarrhythmics.

The term "hemolysis" as used herein refers to a phenomenon in which a membrane of an erythrocyte is broken and hemoglobin and the like contained in the erythrocyte are release to the outside of the erythrocyte.

As used herein the term "neoplastic disease or disorder" refers to cancer as well as other diseases caused by malignant or benign tumors. "Neoplastic diseases" are characterized by abnormal tissue that shows partial or complete lack of structural organization and functional coordination with normal tissue, and usually forms a distinct mass which may be either benign or malignant.

The term "neurodegenerative disease" as used herein describes a disease or condition of the nervous system in which the nervous system often deteriorates over time, thus impairing the patient from carrying out normal tasks including motor tasks and tasks related to cognition and/or memory. "Neurodegenerative diseases" include, for example, Parkinson's disease, Huntington disease, Alzheimer's disease and related disorders such as amyotrophic lateral sclerosis, spinal muscular atrophy, Friedrich's ataxia, Pick's disease, Bassen-Kornzweig syndrome, Refsom's disease, retinal degeneration, Cruetzfelt-Jacob syndrome or prion disease (mad cow disease), dementia with Lewy bodies, schizophrenia, paraneoplastic cerebellar degeneration and neurodegenerative conditions caused by stroke, among others.

The term "Alzheimer's disease" (abbreviated herein as "AD") as used herein refers to a condition associated with formation of neuritic plaques comprising, β-amyloid protein primarily in the hippocampus and cerebral cortex, as well as impairment in both learning and memory. "AD" as used herein is meant to encompass both AD as well as AD-type pathologies. As used herein, the term "Parkinson's disease" refers to a neurological syndrome usually resulting from a dopamine deficiency, resulting from degenerative, vascular, or inflammatory changes in the basal ganglia of the substantia nigra.

The term "macular degeneration" refers to any of a number of conditions in which the retinal macula degenerates or becomes dysfunctional, e.g., as a consequence of decreased growth of cells of the macula, increased death or rearrangement of the cells of the macula (e.g., RPE cells), loss of normal biological function, or a combination of these events. Macular degeneration results in the loss of integrity of the histoarchitecture of the cells and/or extracellular matrix of the normal macula and/or the loss of function of the cells of the macula. Examples of macular degeneration-related disorder include AMD, North Carolina macular dystrophy, Sorsby's fundus dystrophy, Stargardt's disease, pattern dystrophy, Best disease, dominant drusen, and Malattia Leventinese (radial drusen). The term also encompasses extramacular changes that occur prior to, or following dysfunction and/or degeneration of the macula. Thus, the term "macular degeneration" also broadly includes any condition which alters or damages the integrity or function of the macula (e.g., damage to the RPE or Bruch's membrane). For example, the term encompasses retinal detachment, chorioretinal degenerations, retinal degenerations, photoreceptor degenerations, RPE degenerations, mucopolysaccharidoses, rod-cone dystrophies, cone-rod dystrophies and cone degenerations.

As used herein the term "cataract" refers to any opacification of the natural crystalline lens in the eye. Cataracts cause loss of vision.

The term "liposome" as used herein refers to and includes uni- and multi-lamellar vesicles and lipid emulsions. The "liposome" is a capsule or a structure wherein the wall or membrane thereof is formed of lipids, especially phospholipid, with the optional addition therewith of a sterol, especially cholesterol.

The term "in vivo" refers to within the body or in body fluids that normally circulate entirely within the body within its own protective skin, such as the blood, the lymph, or the interstitial fluid. The term "in vitro" refers to a reaction/a process/a phenomenon occurring outside of a body or a living organism.

As used herein, the terms "subject" or "patient" are intended to include living organisms that may have one or more conditions referred to herein. Examples of subjects include humans, monkeys, horses, cows, sheep, goats, dogs, cats, mice, rats, and transgenic species thereof. Other examples of subjects include experimental animals such as mice, rats, dogs, cats, goats, sheep, pigs, and cows. A subject can be a human suffering from or suspected of having, against a one or more proliferative diseases.

The term "systemic administration" as used herein refers to oral, sublingual, buccal, transnasal, transdermal, rectal, intramuscular, intravenous, intraventricular, intrathecal, and subcutaneous routes.

The term "intravenous administration" includes injection and other modes of intravenous administration.

The terms "administration of" or "administering a" compound refers to providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

Techniques and compositions for making useful dosage forms using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions of each incorporated herein by reference.

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "effective amount" or "therapeutically effective amount" indicates the amount of the subject compound that will elicit the biological or medical response of a tissue, system, animal or human that is being sought by the researcher, veterinarian, medical doctor or other clinician.

As used herein, the term "treatment" or "treating" includes any administration of a compound of the present invention and further includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

This invention comprises a method for treating systemic diseases characterized by abnormal cellular stimuli, pathologic responses to oxidants, cytokines, and growth factors; leading to abnormal activation of signaling pathways, protein synthesis and unfettered death or proliferation. Blocking these pathways at one or more sites is a preferred therapeutic method and, curcumin has been chosen to accomplish this. To render the molecule soluble in blood, and to avoid negligible bioavailability due to intestinal wall and hepatic inactivation using the oral route, intravenous liposomal, nanopolymeric, and PLGA curcumin formulations have been devised. Toxicological studies in four dogs following a one hour intravenous infusion at 440 mg/M$^2$ revealed a single episode of reversible red blood corpuscle or cell (RBC) hemolysis and hematuria. Higher doses induced severe irreversible hemolysis. Extrapolation to humans assuming human red blood corpuscles are similarly sensitive to curcumin's hemolytic effects suggest an infusion of less than 440 mg/M$^2$ ($C_{max}$ of 160 ug/mL) would fall below the RBC hemolytic threshold The hemolytic mechanism of action is curcumin induced intracellular influx of calcium ions which leads to RBC membrane rupture and consequent hemolysis. This invention comprises an antidote for this action by pre- or concomitant administration of a calcium channel blocker.

The invention is generally in the field of curcumin administration, the active principle of the turmeric plant, which has been synthesized to near purity (99.2%)[1]. It is formulated with liposomes[2], polymers[3], or PLGA[4] to render it capable of being administered intravenously as a bolus or as a continuous infusion over 1-72 hours in combination with a calcium channel blocker. Curcumin has antioxidant and anti-inflammatory activity, and can block autonomous intracellular signaling pathways abnormally responsive to extracellular growth factors, uncontrolled proliferation of cells and fibrosis-associated and tissue-degenerative conditions. Specifically, curcumin reacts negatively with components of key signaling pathways commanding proliferation, metabolism, survival and death. Oral and topical administration of the extract of the turmeric plant has been used in traditional medicine for over two thousand years. While oral administration is devoid of systemic toxicity it is also devoid of systemic therapeutic activity[5]. This is due to blood insolubility, and intestinal wall and hepatic inactivation, i.e., it has negligible bioavailability for systemic diseases by the oral route. To overcome these limitations, parenteral intravenous curcumin formulations with liposomes[2], polymers[3] (n-isopropylacrylamide, N-vinylpyrrolidione and acrylic acid) and polylactic glycolic acid copolymer were entered into in preclinical drug development[4].

The present invention allows curcumin to be used intravenous with little or no hemolysis. Curcumin a food chemical present in turmeric (Curcuma longa) has been considered to be pharmacologically safe when taken by the oral route as an extract. Beneficial responses in murine models of disease or murine models incorporating xenotransplanted human tumors has been demonstrated at nontoxic intravenous, or intraperitoneal, or oral dosages.[3] However, following synthesis of near pure curcumin (99.2%), and during conduction of pre-clinical animal toxicity studies in dogs evidence of dose dependent acute hemolysis was observed.[6] The severity of hemolysis ranged from a single episode following a one hour infusion of 400 mg/M$^2$ to irreversible life threatening hemolysis at 800 mg/M$^2$. Significant hemolysis was observed when these observations were extended to in vitro assays measuring hemolysis of human red blood corpuscles following brief exposures to low (less than 10 ug/ml) concentrations of liposomal curcumin. These data indicate serious hemolytic issues, which prohibit translational efficacy of intravenous curcumin treatment of neoplastic, parasitic and tissue-degenerative diseases. More importantly, these data contradict the implied assumption of safety if curcumin is administered intravenously to dogs and to humans. The current art is deficient in clinical strategies that allow intravenous administration of curcumin. The dose finding trials with the observed adverse hemolytic reactions in dogs are the first reported.[9] Because the mechanism of RBC hemolysis is intimately tied to $Ca^{++}$ imbalance, the resolution for safe administration, i.e. the present invention, consists of sustained intravenous administration at sub-hemolytic dosages in combination with correction of curcumin induced intracellular Ca++ imbalances with a calcium blocking agent. This invention fulfills a need in the art of translating important toxicological observations in in vitro and animal models of disease to humans.

Dosage of intravenous curcumin: In human pancreatic tumor xenografts in mice, the optimum intravenous dosage 125 mg/M² (with a blood $C_{max}$ of 200 ug/ml) three times weekly for four weeks[8]. In mice and rats no adverse events were observed in dose-finding studies of intravenous liposomal curcumin at 250 mg/M², the maximum injectible volume due to solubility limitations. However, in three of four dogs, acute reversible hemolysis and hematuria followed 440 mg/M² liposomal curcumin infused over one hour. At higher curcumin dosages acute hemolysis was severe, and life threatening[6]. Extrapolating to humans and assuming similar drug metabolism, distribution and pharmacokinetics these data suggest that a 440 mg/M² (blood $C_{max}$ of 160 ug/ml) one hour infusion of curcumin in an 80 kg human may induce acute reversible hemolysis where the human RBC is more sensitive than the dogs. This suggests that dosages inducing blood dosage and $C_{max}$ be carefully titrated when developing intravenous curcumin in any of the formulations. Comparison of dose/body weight and dose/body surface area in mice, rats, dogs, and humans are shown in Table I.

The mechanism of adverse reaction: The most probable mechanism, but in no way a limitation of the present invention, by which curcumin induces hemolysis is oxidation of calcium ATPase reactive —SH groups which leads to complete inhibition of enzyme activity, changes in $Ca^{++}$ permeability ion channels, and collapse of the gradient between external ($10^{-3}$M) and intracellular ($<10^{-5}$M) calcium. This leads to enhanced $Ca^{++}$ influx[12], which in turn induces phospholipid perturbations of the red blood corpuscle outer membrane leading to membrane lysis and hemolysis.[7] This invention proposes a method to limit exacerbated $Ca^{++}$ influx induced by curcumin and thus to mitigate hemolytic effects from intravenous curcumin administration by concomitant administration of a Ca channel blocker. This would apply to twice weekly PLGA-nanocurcumin[4], a sustained-release formulation or slow intravenous infusions of liposomal curcumin or polymeric nanocurcumin.

Rational for intravenous administration: Intravenous administration of liposomal curcumin offers direct distribution to pathologic tissues prior to passage and metabolism in the hepatic circulation, and may permit preferential accumulation of active principle in tumor or degenerated cells compared to normal cells. These factors plus potential additional protection from hepatic inactivation by the polymeric or sustained release PLGA nanocurcumin formulations make this invention an improvement over oral and topical methods of administration[8,9,10]. It is an objective of the present invention to provide a protracted exposure of curcumin and concomitantly a calcium channel blocker as a method of treating humans with cell/tissue proliferative and neurodegenerative disorders characterized by growth receptor and signaling pathway dysfunctions.

Extrapolation from animal toxicology: In dogs one-hour intravenous administration of liposomal curcumin at 440 mg/M²($C_{max}$ 200 ug/ml) was followed by reversible hemolysis within 24 hours. A single one-hour infusion of 800 mg/M² ($C_{max}$ 400 ug/mL) liposomal curcumin was followed by irreversible hemolysis and life threatening anemia[6]. Extrapolating to humans from the dog, $C_{max}$ in the blood should not surpass $C_{max}$ 200 ug/ml (following 300 mg/M²) to avoid hemolysis. Curcumin induced hemolysis can theoretically be partially resolved by sustained release from PLGA curcumin, or constant infusion of liposomal or polymeric nanocurcumin dosages below 300 mg/M². In vitro hemolysis of RBC comparing liposomal curcumin and curcumin in humans and dogs are presented in Table II.

Extrapolation from in vitro toxicity: Everett et al., reported turmeric extract (78% curcumin) at 1-10 uM (0.368-3.68 ug/ml) induced apoptosis in human cultured primary leukemic B-CLL cells. The $EC_{50}$ was optimal at 24-48 hours exposure.[11] Based upon these observations, in humans, 9 mg/M² intravenously in an 80 kg person would produce a $C_{max}$ blood level of 3.4 ug/ml. To achieve a steady state at this level, assuming the T/2 in humans is three hours a 24 hour infusion of liposomal curcumin or polymeric nanocurcumin, would require a 384 mg constant infusion concentration of liposomal curcumin infused over 24 hours or longer. Infusions of this concentration and rate will fall below the 10 ug/ml hemolytic dose, and below the $EC_{50}$ of 21.8 uM for non-malignant human mononuclear cells[11]. Translating to the clinical level with PLGA curcumin this invention proposes a four week treatment cycle with 2,700 mg weekly. The rational for concomitant calcium channel blocker administration is the differential in sensitivity to curcumin effects on $Ca^{++}$ influx in nucleated hematopoietic cells and red blood corpuscles and one of several classes of calcium channel blockers, which disrupt the conduction of calcium channels leading to a decrease in intracellular calcium hence preventing the initiation of the hemolysis cascade. The curcumin induction of hemolysis is considered to be initiated by increased calcium ion transport to the RBC interior following inhibition of $calcium^{++}$ ATPase. With the opening of the $Ca^{++}$ permeability channels the influx of $Ca^{++}$ activates RBC membrane scramblase leading to movement of phosphatidylserine to the outer membrane leaflet. This is followed by RBC membrane lysis, cell shrinkage and hemoglobin release. This invention teaches a combination of sustained sub-hemolytic dosages of curcumin combined with a calcium channel blocker to prohibit adverse hemolytic effects.

TABLE I

Comparison of dose/body weight and dose/body surface area in mice, rats, dogs, and humans.

| Species | Body Weight | Body Surface Area (M²) | |
|---------|-------------|------------------------|---|
| Mouse | 20 grams | 0.03 | dosing at 40 mg/kg bolus = 0.8 mg/0.003M² = 250 mg/M² |
| | | | dosing at 20 mg/kg bolus = 0.4 mg/0.003M² = 125 mg/M² |
| Rat | 250 grams | 0.035 | dosing at 40 mg/kg bolus = 10 mg/0.035M² = 300 mg/M² |
| Dog | 10 kilograms | 0.46 | dosing at 40 mg/kg/hour = 400 mg/0.46M² = 800 mg/M² |
| | | | dosing at 15 mg/kg/hour = 150 mg/0.46M² = 300 mg/M² |

TABLE I-continued

Comparison of dose/body weight and dose/body surface area in mice, rats, dogs, and humans.

| Species | Body Weight | Body Surface Area (M$^2$) | |
|---|---|---|---|
| Human | 80 kilograms | 1.8 | dosing at 7.0 mg/kg/hour = 560 mg/1.8M$^2$ = 300 mg/M$^2$ |
| | | | dosing at 3.0 mg/kg/hour = 240 mg/1.8M$^2$ = 125 mg/M$^2$ |

TABLE II

In vitro hemolysis of RBC comparing liposomal curcumin and curcumin.

| | Curcumin Liposomal (mcg) | | | Curcumin-ETOH (mcg) | |
|---|---|---|---|---|---|
| | 400 | 150 | 10 | 400 | 10 |
| Human RBC % hemolysis | 59.8 | 54.5 | 44 | 66.9 | 57.6 |
| Canine RBC % hemolysis | 30.4 | 3.3 | 2.7 | 4.2 | 0.5 |

A skilled in the art will acknowledge readily that the present invention is well designed to carry out the advantages of intravenous curcumin formulations while avoiding hemolysis a critical adverse reaction that will prohibit translation to human diseases and conditions otherwise amenable to curcumin therapy. The present methods and specific compounds described herein are presently representative of preferred embodiments, are exemplary, and are not intended as limitations on the scope of the invention. Changes to this invention and other uses will occur to those skilled in the art, which are encompassed within the spirit of the invention as defined by the scope of the claims.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,723,515: Methylene Blue—Curcumin Analog for The Treatment of Alzheimer's Disease.
U.S. Patent Application No. 20060067998: Liposomal Curcumin for Treatment of Cancer.

1. Muhammed Majeed PhD, C.E.O. Sabinsa Inc. Piscataway, N.J., USA.
2. Dietmar Katinger M S. Director Polymun Inc, Vienna, Austria.
3. Bisht S, Feldman F, Soni S, Ravi R, Karikar C, Maitra A 2007 Polymeric nanoparticles encapsulated curcumin ('nanocurcumin'):a novel strategy for human cancer therapy, J Nanobiotech 5: 3.
4. Mukerjee A and Jamboor K, Vishwanatha, 2009 Formulation, Characterization and Evaluation of Curcumin-loaded PLGA Nanosphers for cancer therapy Univ. Anticancer Reasearch 29:3867-3876.
5. Aggarwal B, B, et al The molecular targets and therapeutic uses of curcumin in health and disease, 2006, Springer pp 1-481.
6. Smith, J. A. M.D. Anderson Cancer Center, Houston Tex., USA unpublished data.
7. Bentzen, P et al. (2007) Curcumin Induced Suicidal Erythrocyte Death. Cell Physiol Biochem 19:153-164.
8. Mach C. M. et al 2009. Determination of minimum effective dose and optimal dosing schedule for liposomal curcumin in a xenografts human pancreatic cancer model. Journal of Anticancer research. 29:1895-1900.
9. Smith J. A., Mathew L., Mach, C. M, Santiago K, Helson L. 2009 Development of liposomal curcumin as a new potential anticancer agent. Abstract: AACR EORTC NCI, Boston Mass. November 17.
10. Lan Li, Fadi S, Braiteh F. S, Razelle Kurzock 2005, Liposome encapsulated curcumin, in vitro and in vivo effects on proliferation, apoptosis, signaling and angiogenesis. Cancer 104: 1322-1331.
11. Everett P. C et al 2006. Preclinical assessment of curcumin as a potential therapy for B-CLL. Am. J. Hematology 82:1-8.
12. Logan-Smith M. J. Lockyer P. J, East J. M, and A. G Lee, 2001 Curcumin, a molecule that inhibits the $Ca^{2+}$-ATPase of Sarcoplasmic Reticulum but Increases the Rate of Accumulation of $Ca^{2+}$ J. Biol Chemistry 276:46905-4691.

What is claimed is:

1. A method comprising intravenous administration to a subject of a therapeutically effective amount of an intravenous composition of curcumin, wherein the curcumin is enveloped by a polylactic glycolic acid (PLGA) copolymer and a layer of lipids to form a liposome, with one or more calcium channel blockers to mitigate intravenous curcumin induced red blood cell (RBC) hemolysis.

2. The method of claim 1, wherein the one or more calcium channel blockers are selected from the group consisting of verapamil, ethylisopropylameloride, niflamic acid, NPPB, dihydropyridines, phenylalkylamines, Benzothiozepines, Diltiazem, nonselective blockers comprising mibefradil, bepridil, fendeline, fluspirilene, catecholamines, and erythropoietin.

* * * * *